United States Patent
Ghirardini et al.

(10) Patent No.: US 9,006,476 B2
(45) Date of Patent: Apr. 14, 2015

(54) PROCESS FOR THE PRODUCTION OF HIGH-PURITY DIMETHYL CARBONATE

(75) Inventors: Maurizio Ghirardini, Milan (IT); Laura De Nardo, Monza (IT); Elena Novello, Cernusco sul Naviglio (IT)

(73) Assignee: versalis S.p.A., San Donato Milanese (IT)

( * ) Notice: Subject to any disclaimer, the term of this patent is extended or adjusted under 35 U.S.C. 154(b) by 96 days.

(21) Appl. No.: 13/508,171

(22) PCT Filed: Oct. 29, 2010

(86) PCT No.: PCT/IB2010/002776
§ 371 (c)(1),
(2), (4) Date: Jul. 18, 2012

(87) PCT Pub. No.: WO2011/055204
PCT Pub. Date: May 12, 2011

(65) Prior Publication Data
US 2012/0283464 A1    Nov. 8, 2012

(30) Foreign Application Priority Data
Nov. 4, 2009    (IT) .............................. MI 2009 A 1927

(51) Int. Cl.
*C07C 68/08* (2006.01)
*C07C 69/96* (2006.01)

(52) U.S. Cl.
CPC ...................................... *C07C 68/08* (2013.01)

(58) Field of Classification Search
None
See application file for complete search history.

(56) References Cited

U.S. PATENT DOCUMENTS

2005/0080274 A1    4/2005    Miyake et al.

FOREIGN PATENT DOCUMENTS

| CN | 1944392 | 4/2007 |
|---|---|---|
| EP | 1 460 056 | 9/2004 |
| KR | 10 0713141 | 5/2007 |

OTHER PUBLICATIONS

Machine translation of CN 1944392, Accessed Jan. 25, 2014; obtained from espacenet <http://worldwide.espacenet.com/?locale=en_EP>.*
Machine translation of KR 10-0713141, Accessed Jan. 25, 2014; obtained from K-PION <http://kposd.kipo.go.kr:8088/up/kpion/>.*
Delledonne, D., et al., "Developments in the production and application of dimethylcarbonate," Applied Catalysis A: General, vol. 221, pp. 241-251, (2001).
International Search Report Issued Jan. 18, 2011 in PCT/IB10/02776 Filed Oct. 29, 2010.

* cited by examiner

*Primary Examiner* — Alicia L Otton
(74) *Attorney, Agent, or Firm* — Oblon, McClelland, Maier & Neustadt, L.L.P.

(57) ABSTRACT

A process for producing a high-purity dimethyl carbonate, which includes: (I) cooling a commercial grade dimethyl carbonate containing 1 ppm or more of chlorine to a temperature from +6° C. to −5° C. at a rate from 0.5-2° C./hour, to obtain a first solid dimethyl carbonate; (II) heating the first solid dimethyl carbonate to a temperature from −5° C. to +6° C. at a rate of 1-5° C./hour, to obtain a mixture comprising a second solid dimethyl carbonate and a predetermined amount of a first liquid dimethyl carbonate; (III) separating the first liquid dimethyl carbonate from the mixture, to obtain the second solid dimethyl carbonate; (IV) heating the second solid dimethyl carbonate to a temperature from 20° C. to 40° C., to obtain a second liquid dimethyl carbonate, wherein the second liquid dimethyl carbonate has a purity degree higher than 99.99% and a chlorine content lower than or equal to 1 ppm.

15 Claims, 1 Drawing Sheet

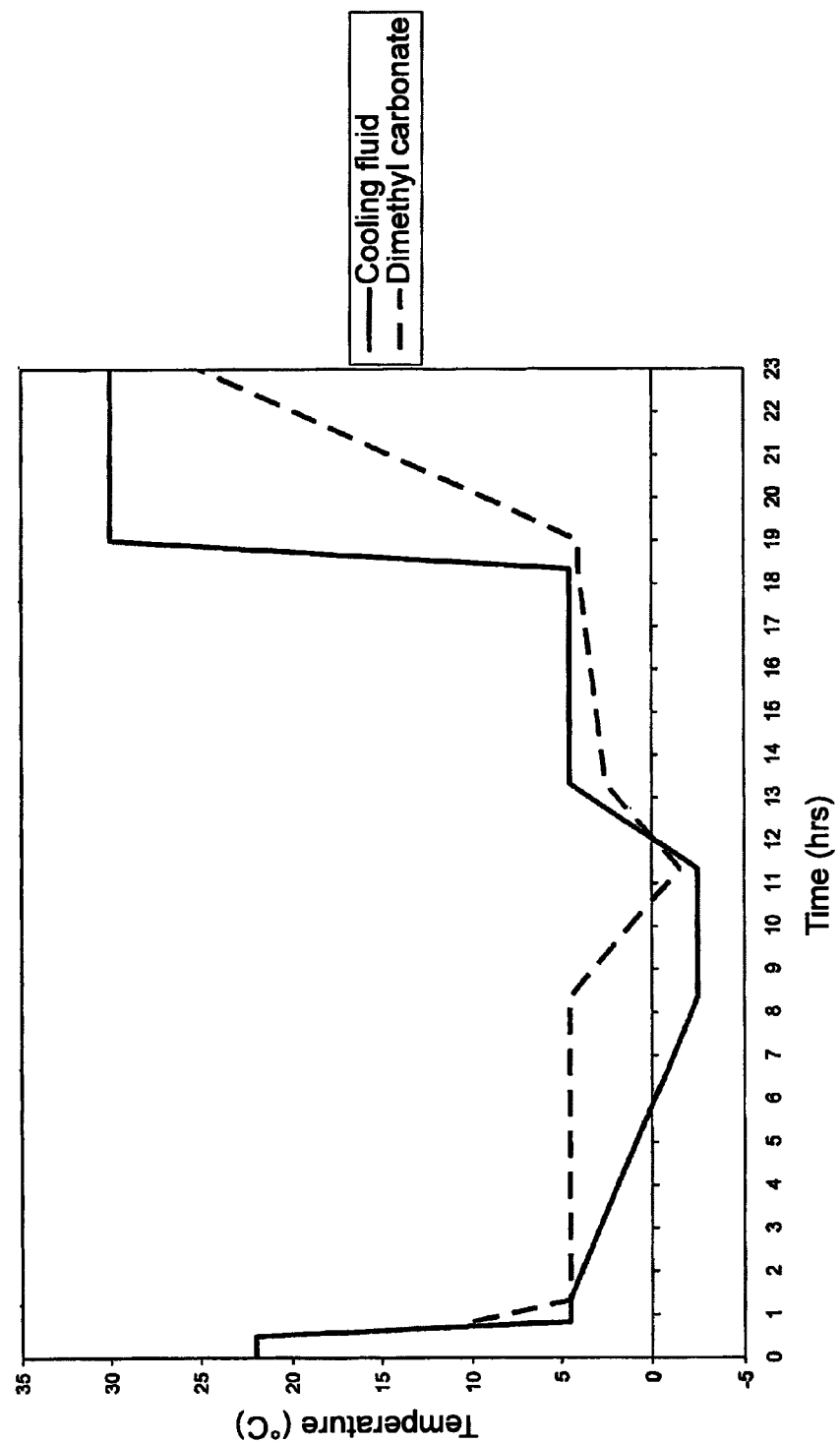

PROCESS FOR THE PRODUCTION OF HIGH-PURITY DIMETHYL CARBONATE

The present invention relates to a process for the production of a high-purity dimethyl carbonate.

More specifically, the present invention relates to a process for the production of a high-purity dimethyl carbonate, comprising subjecting dimethyl carbonate to a cooling and heating cycle, operating under particular temperature conditions and under particular cooling and heating rates.

Said dimethyl carbonate is particularly useful as organic solvent in the electronic industry, more specifically, as organic solvent for the production of the electrolyte of lithium batteries.

The present invention also relates to the use of dimethyl carbonate obtained from the above-mentioned process as organic solvent in the electronic industry, more specifically as organic solvent for the production of the electrolyte of lithium batteries.

It is known that dialkyl carbonates are important intermediates for the synthesis of fine chemicals, pharmaceutical products and plastic materials and are useful as synthetic lubricants, solvents, plasticizers, monomers for organic glasses and various polymers, among which polycarbonates.

In particular, thanks to its low toxicity and to its low reactivity, dimethyl carbonate (DMC) can be used as fluid with a low environmental impact in numerous applications which require the presence of a solvent, for example, as a substituent of solvents containing fluorine, used in the electronic industry.

It is known that application in electronics, in particular as solvent for the production of the electrolyte of lithium batteries, requires the use of high-purity dimethyl carbonate, i.e. higher than 99.99%.

In this respect, processes are known in the art for the production of high-purity dimethyl carbonate.

The Chinese patent application 1,944,392, for example, describes a process for the purification of high-purity dimethyl carbonate comprising: cooling a commercial grade dimethyl carbonate to a temperature of 4° C. (i.e. the temperature corresponding to the melting point of dimethyl carbonate) in order to obtain a crystalline solid; stopping the cooling when the crystalline solid has reached a predetermined amount obtaining a solid/liquid mixture; eliminating the liquid present in said solid/liquid mixture obtaining a crystalline solid; heating said crystalline solid obtaining a liquid product, i.e. a dimethyl carbonate having a purity degree higher than 99.99%. The dimethyl carbonate obtained with the above process is said to be useful as solvent for the production of the electrolyte of lithium batteries.

Korean patent application KR 713141 describes a process for obtaining a high-purity dimethyl carbonate comprising the following steps: cooling a starting material comprising at least 85% by weight of a dimethyl carbonate obtained by the transesterification of alkylene carbonate with methanol, passing from room temperature to a temperature ranging from −5° C. to −25° C., at a cooling rate ranging from 0.05° C./min to 0.7° C./min, so as to obtain crystallization in the absence of solvent; heating the crystals obtained from said crystallization to a temperature ranging from 10° C. to 20° C., at a heating rate ranging from 0.1° C./min to 0.5° C./min, so as to partially melt said crystals and, at the same time, to remove the impurities contained in said crystals, obtaining a dimethyl carbonate having a purity degree higher than at least 99%.

The above procedures, however, make no reference to the amount of chlorine present in the dimethyl carbonate obtained.

The Applicant has considered the problem of finding a process for the production of dimethyl carbonate having, in addition to a high purity, i.e. having a purity degree higher than 99.99%, a chlorine content lower than or equal to 1 ppm.

The Applicant has now found that by subjecting dimethyl carbonate to a cooling and heating cycle, operating under particular temperature conditions and under particular cooling and heating rates, a dimethyl carbonate can be obtained having not only a purity degree higher than 99.99% (i.e. with a high purity), but also a chlorine content lower than or equal to 1 ppm. The high purity degree and the extremely low chlorine content (i.e. lower than or equal to 1 ppm) make said dimethyl carbonate particularly suitable as organic solvent in the electronic industry, more specifically, as organic solvent for the production of the electrolyte of lithium batteries.

An object of the present invention therefore relates to a process for the production of high-purity dimethyl carbonate comprising:
  subjecting at least one commercial grade dimethyl carbonate, having a chlorine content higher than 1 ppm, preferably ranging from 10 ppm to 100 ppm, to cooling, operating at a cooling temperature ranging from +6° C. to −5° C., preferably ranging from +5° C. to −3° C., and at a cooling rate ranging from 0.5° C./hour to 2° C./hour, preferably ranging from 0.8° C./hour to 1.5° C./hour, so as to obtain dimethyl carbonate in solid form;
  subjecting said dimethyl carbonate in solid form to a first heating, operating at a heating temperature ranging from −5° C. to +6° C., preferably ranging from −3° C. to +5° C., and at a heating rate ranging from 1° C./hour to 5° C./hour, preferably ranging from 1.5° C./hour to 4° C./hour, so as to obtain a mixture comprising dimethyl carbonate in solid form and a predetermined amount of dimethyl carbonate in liquid form;
  separating said dimethyl carbonate in liquid form from said mixture in order to obtain dimethyl carbonate in solid form;
  subjecting said dimethyl carbonate in solid form to a second heating, operating at a heating temperature ranging from 20° C. to 40° C., preferably ranging from 25° C. to 35° C., so as to obtain dimethyl carbonate in liquid form, said dimethyl carbonate in liquid form having a purity degree higher than 99.99% and a chlorine content lower than or equal to 1 ppm.

For the purpose of the present description and of the following claims, the definitions of the numerical ranges always include the extremes, unless otherwise specified.

For the purpose of the present description and of the following claims, the term "commercial grade" refers to a dimethyl carbonate having a purity degree ranging from 98% to 99.95%.

For the purpose of the present description and of the following claims, the term "cooling temperature" refers to the temperature of the cooling fluid used for the purpose of the process of the present invention.

For the purpose of the present description and of the following claims, the term "heating temperature" refers to the temperature of the cooling fluid used for the purpose of the process of the present invention.

According to a preferred embodiment of the present invention, said cooling can be, carried out for a time ranging from 1 hour to 20 hours, preferably ranging from 5 hours to 15 hours.

According to a preferred embodiment of the present invention, said first heating can be carried out for a time ranging from 2 hours to 10 hours, preferably ranging from 3 hours to 8 hours.

According to a preferred embodiment of the present invention, said first heating can start when the commercial grade dimethyl carbonate subjected to said cooling has reached a temperature higher than or equal to −2° C., preferably ranging from −1.8° C. to −1° C.

According to a preferred embodiment of the present invention, said dimethyl carbonate in liquid form can be present in the mixture obtained after said first heating, in an amount ranging from 15% by weight to 30% by weight, preferably ranging from 18% by weight to 25% by weight, with respect to the total weight of the starting commercial grade dimethyl carbonate.

It should be noted that the chlorine contained in the starting commercial grade dimethyl carbonate prevalently remains in the dimethyl carbonate in liquid form present in the mixture obtained after said first heating.

According to a preferred embodiment of the present invention, the dimethyl carbonate in liquid form present in the mixture obtained after said first heating, is a dimethyl carbonate having a chlorine content higher than or equal to 4 ppm, preferably ranging from 40 ppm to 500 ppm.

The separation of the dimethyl carbonate in liquid form from the dimethyl carbonate in solid form, both present in the mixture obtained after said first heating, is carried out by discharging said dimethyl carbonate in liquid form from the equipment used for the above-mentioned process.

The above process can be carried in equipment known in the art, such as, for example, heat exchangers, in particular in heat exchangers equipped with finned tubes.

The present invention also relates to the use of dimethyl carbonate obtained according to the process described above, as organic solvent in the electronic industry, in particular as organic solvent for the production of the electrolyte of lithium batteries.

Some illustrative and non-limiting examples are provided below for a better understanding of the present invention and for its embodiment.

EXAMPLE 1

4450 kg of commercial grade dimethyl carbonate, having a purity degree of 99.9% and a chlorine content of 15 ppm, were fed, from the shell side, to a heat exchanger equipped with finned tubes. The tube side, on the other hand, is connected to a cooling system capable of controlling the temperature of the cooling fluid which is inside the finned tubes.

During the feeding, the cooling fluid was maintained at 22° C. At the end of the feeding, after 30 minutes, the cooling fluid was cooled to a temperature of 4.5° C. in 20 minutes, and the dimethyl carbonate was left at this temperature for 30 minutes.

The cooling fluid was subsequently further cooled to a temperature of −2.5° C., in 7 hours, operating at a cooling rate of 1° C./h, and the dimethyl carbonate is left at this temperature for 3 hours. At the end, the dimethyl carbonate reaches a temperature of −1.5° C. and is in the form of a solid.

Subsequently, the cooling fluid was heated to a temperature of 4.5° C., in 2 hrs, operating at a heating rate of 3.5° C./h and the dimethyl carbonate was left at this temperature for 5 hours, obtaining a mixture comprising liquid dimethyl carbonate (22.4% by weight with respect to the total weight of the starting dimethyl carbonate) and solid dimethyl carbonate. The liquid dimethyl carbonate, having a chlorine content of 70 ppm, was discharged from the heat exchanger.

The cooling fluid was then heated to a temperature of 30° C., in 40 minutes, and the dimethyl carbonate is left at this temperature for 4 hrs, obtaining liquid dimethyl carbonate.

The liquid dimethyl carbonate obtained, having a purity degree of 99.99% and a chlorine content of less than 1 ppm, was discharged from the heat exchanger.

The purity degree was determined by means of gas chromatographic analysis, whereas the chlorine content was determined according to the standard ASTM D4929-07 (Method B).

FIG. 1 shows the trend of the temperature of the cooling fluid and of the temperature of the dimethyl carbonate during the process described above: the ordinate indicates the temperature in ° C. and the abscissa the time in hours.

The invention claimed is:

1. A process for producing a high-purity dimethyl carbonate, the process comprising:
    (I) cooling a commercial grade dimethyl carbonate comprising more than 1 ppm of chlorine by operating a cooling fluid at a cooling temperature ranging from +6° C. to −5° C. at a cooling rate ranging from 0.5° C./hour to 2° C./hour, to obtain a first dimethyl carbonate in solid form;
    (II) heating the dimethyl carbonate in solid form, in a first heating, by operating the cooling fluid at a heating temperature ranging from −5° C. to +6° C. at a heating rate ranging from 1° C./hour to 5° C./hour, to obtain a mixture comprising a second dimethyl carbonate in solid form and a predetermined amount of a first dimethyl carbonate in liquid form, wherein the first dimethyl carbonate in liquid form is present in the mixture in an amount ranging from 15% to 30% by weight with respect to a total weight of the commercial grade dimethyl carbonate;
    (III) separating the first dimethyl carbonate in liquid form from the mixture, to obtain the second dimethyl carbonate in solid form; and
    (IV) heating the second dimethyl carbonate in solid form, in a second heating, by operating the cooling fluid at a heating temperature ranging from 20° C. to 40° C., to obtain a second dimethyl carbonate in liquid form, wherein the second dimethyl carbonate in liquid form has a purity degree higher than 99.99% and a chlorine content lower than or equal to 1 ppm.

2. The process of claim 1, wherein the commercial grade dimethyl carbonate has a chlorine content in a range from 10 ppm to 100 ppm.

3. The process of claim 1, wherein the cooling (I) is carried out at a temperature in a range from +5° C. to −3° C. and wherein the heating (II) is carried out at a temperature in a range from −3 C to +5 C.

4. The process of claim 1, wherein the cooling (I) is carried out at a cooling rate in a range from 0.8° C./hour to 1.5° C./hour.

5. The process of claim 1, wherein the heating (II) is carried out at a heating rate in a range from 1.5° C./hour to 4° C./hour.

6. The process of claim 1, wherein the heating (IV) is carried out at a temperature in a range from 25° C. to 35° C.

7. The process of claim 1, wherein cooling (I) is carried out for a time in a range from 1 hour to 20 hours.

8. The process of claim 7, wherein the cooling (I) is carried out for a time in a range from 5 hours to 15 hours.

9. The process of claim 1, wherein the heating (II) is carried out for a time in a range from 2 hours to 10 hours.

10. The process of claim 9, wherein the heating (II) is carried out for a time in a range from 3 hours to 8 hours.

11. The process of claim 1, wherein the heating (II) starts before the commercial grade dimethyl carbonate in the cooling (I) has reached a temperature lower than −2° C.

12. The process of claim 11, wherein the heating (II) starts when the commercial grade dimethyl carbonate in the cooling (I) has reached a temperature in a range from −1.8° C. to −1° C.

13. The process of claim 1, wherein the first dimethyl carbonate in liquid form is present in the mixture obtained after the heating (II) in an amount in a range from 18% to 25% by weight, with respect to a total weight of the commercial grade dimethyl carbonate.

14. The process of claim 1, wherein the first dimethyl carbonate in liquid form present in the mixture obtained after the heating (II) has a chlorine content higher than or equal to 4 ppm.

15. The process of claim 14, wherein the first dimethyl carbonate in liquid form present in the mixture obtained after the heating (II) has a chlorine content in a range from 40 ppm to 500 ppm.

\* \* \* \* \*